United States Patent
Krishna et al.

(10) Patent No.: US 9,314,027 B2
(45) Date of Patent: *Apr. 19, 2016

(54) FUNCTIONALIZED FULLERENES AS ANTIFUNGAL AGENTS

(75) Inventors: Vijay Krishna, Gainesville, FL (US); Brij M. Moudgil, Gainesville, FL (US); Benjamin L. Koopman, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 17 days.

This patent is subject to a terminal disclaimer.

(21) Appl. No.: 13/258,649

(22) PCT Filed: Apr. 1, 2010

(86) PCT No.: PCT/US2010/029650
§ 371 (c)(1),
(2), (4) Date: Sep. 22, 2011

(87) PCT Pub. No.: WO2010/115013
PCT Pub. Date: Oct. 7, 2010

(65) Prior Publication Data
US 2012/0015045 A1    Jan. 19, 2012

Related U.S. Application Data

(60) Provisional application No. 61/165,962, filed on Apr. 2, 2009.

(51) Int. Cl.
*A01N 45/00* (2006.01)
*A01N 59/16* (2006.01)
*C01B 31/02* (2006.01)

(52) U.S. Cl.
CPC ............ *A01N 45/00* (2013.01); *C01B 31/0213* (2013.01)

(58) Field of Classification Search
CPC ....... A01N 45/00; A01N 25/00; A01N 59/00; C01B 31/0213
See application file for complete search history.

(56) References Cited

U.S. PATENT DOCUMENTS 5,648,523 A * 7/1997 Chiang .................... 562/100
5,994,410 A * 11/1999 Chiang et al. .............. 514/709
2002/0037383 A1 * 3/2002 Spillman et al. ........... 428/36.91
2005/0181067 A1 * 8/2005 Yokoyama et al. ........... 424/641
2009/0076115 A1 * 3/2009 Wharton et al. .............. 514/410

FOREIGN PATENT DOCUMENTS

WO    WO 2006028297 A1 *  3/2006

OTHER PUBLICATIONS

Fileti et al (Effects of hydroxyl group distribution on the reactivity, stability and optical properties of fullerenols, Published Jul. 28, 2008, Nanotechnology, vol. 19, pp. 1-7).*
Kokubo et al. (Facile Synthesis of Highly Water-Soluble Fullerenes More than Half-Covered by Hydroxyl Groups, Jan. 10, 2008, vol. 2, pp. 327-333).*
Tegos et al (Chem Biol., Oct. 2005, vol. 12, pp. 1127-1135 (presented as pp. 1-20)).*
Badireddy et al (Environmental Science Technology, 2007, vol. 41, pp. 6627-6632).*
Akiba et al (J Med Dent Sci, 2005, vol. 52, pp. 223-227).*
EPA report (United States EPA 2007 Progress Report: Microbial Impacts of Engineered Nanoparticles, 2007).*
Tegos, G.P. et al. "Cationic Fullerenes Are Effective and Selective Antimicrobial Photosensitizers" *Chemistry & Biology*, Oct. 2005, 12:1127-1135.
Leal, Jr. S.M. et al., "Fungal antioxidant pathways promote survival against neutrophils during infection," *The Journal of Clinical Investigation*, Jul. 2012, pp. 2482-2498, vol. 122, No. 7.
Ghannoum, M. et al. "Antifungal Agents: Mode of Action, Mechanisms of Resistance, and Correlation of These Mechanisms with Bacterial Resistance" *Clin Microbiol Rev.*, 1999, pp. 501-517, vol. 12, No. 4.

* cited by examiner

*Primary Examiner* — Brian-Young Kwon
*Assistant Examiner* — Mark V Stevens
(74) *Attorney, Agent, or Firm* — Saliwanchik, Lloyd & Eisenschenk

(57) ABSTRACT

Functionalized fullerenes are used in a method of combating fungal growth on surfaces and treating fungal diseases of patients. Surfaces that can be treated by the materials comprising an effective amount of functionalized fullerenes include those of fruits, vegetables, harvested grains, plants, or plant seeds. The method of combating fungal growth on a surface can be augmented but is not dependent on irradiation of the surface by light. Functional fullerenes are employed in various dosage forms such as topical, ingestible or administration.

11 Claims, 1 Drawing Sheet

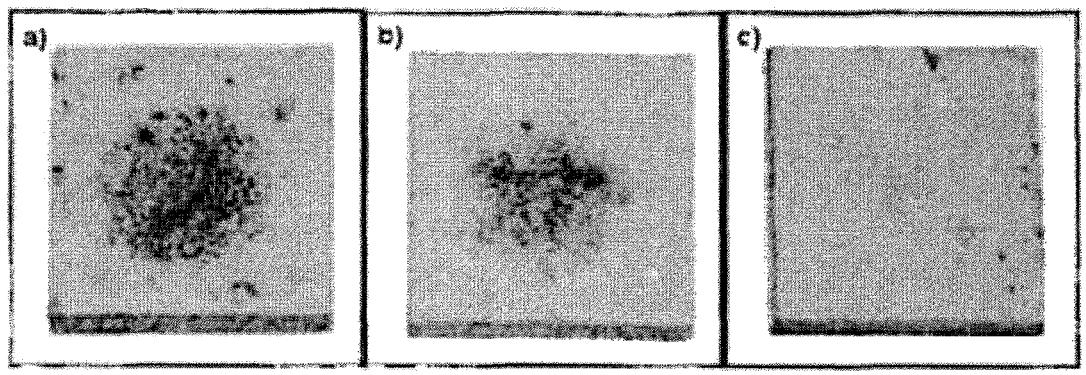

FUNCTIONALIZED FULLERENES AS ANTIFUNGAL AGENTS

CROSS-REFERENCE TO RELATED APPLICATION APPLICATIONS

This application is the U.S. national stage application of International Patent Application No. PCT/US2010/029650, filed Apr. 1, 2010, which claims the benefit of U.S. Provisional Application Ser. No. 61/165,962, filed Apr. 2, 2009, the disclosures of which are hereby incorporated by reference in their entireties, including any figures, tables, or drawings.

BACKGROUND OF INVENTION

Fungi are eukaryotic organisms that are an indispensible part of the ecosystem. Fungi have symbiotic relations with animals and plants, and play a major role in nutrient cycling by decomposing organic matter. Fungi can damage the surfaces of indoor and outdoor structures, and many fungi produce toxins, which affect the health of humans, animals and plants. However, fungi are also highly resistant to microbiological agents, compounds designed to eradicate fungi through the various mechanisms including disrupting reproductive capabilities, destroying cell walls, modifying fungal DNA and disturbing cell function. Fungal infections and infestations in human, animals, plants, and the environment are rising, with many damaging and even lethal consequences. Fungal diseases in plants are responsible for more than $9 billion annual losses in the US; for example, laurel wilt fungus, which kills avocado plants, poses a threat of up to $54 million a year to the Florida avocado industry. Fungal pathogens endanger immuno-compromised patients and are the cause of many emerging infectious diseases, being the third most common life-threatening systemic infection of hospital-bound patients. For these reasons, the global market for antifungal agents that was more than $11 billion in 2007 is expected to reach nearly $14 billion by 2012.

Although fullerenes and functionalized fullerenes are known to have antioxidant activity (e.g. $C_{60}$, $C_{63}(CO_2H)_6$, $C_{60}O$, $C_{60}O_n$, PEG-fullerenes, hydroxy fullerenes, iso-stearate fullerenes), anti-allergic activity (e.g. $C_{60}$) and antiviral activity (e.g. $C_{60}(CH_2)_2N(CH_3)_2^+I^-$, fullerene/PVP complex, $C_{60}C(C_6H_4(CH_2)_2NHC(O)(CH_2)_2OC(O)OH)_2$, $C_{63}(CO_2(CH_2)_3NH_2)_6$) very little literature exists that is directed to antifungal activity of pristine fullerenes and functionalized fullerenes. Tegos et al., *Chemistry & Biology*, 2005, 12 (10): 1127-1135, discloses that fullerenes functionalized with cationic pyrrolidinium groups, $C_{60}(CH_2)_2N(CH_3)_2^+I^-$, can effectively kill fungi but only when illuminated with white light while in the presence of a photosensitizer. The need for light and a photosensitizer does not address the problem of fungal growth in the dark.

BRIEF SUMMARY

Embodiments of the invention are directed to a method of combating fungal growth in the dark or light by providing a material comprising functionalized fullerenes which is distributed over a surface. The functionalized fullerenes can be fullerenes ($C_x$ where x is 20 to 1500) having at least one functional group. The functional groups can independently be attached by one or more covalent bonds, ionic bonds, Dewar coordination, or Kubas interactions. Functional groups can be OH, Br, H, Gd, Ti, or $C(COOH)_2$. The material comprising functionalized fullerenes can also comprise a solvent such as water or an organic liquid. In some embodiments of the invention, the material can include a photocatalyst such as $TiO_2$. In other embodiments the material comprising functionalized fullerenes can include one or more carriers, matrices, additives, excipients or combinations thereof. The method can be used to treat surfaces of fruits, vegetables, harvested grains, plants, or plant seeds.

Other embodiments of the invention are directed to a method of treating a fungal disease where a material comprising functionalized fullerenes can be administered to deliver an effective amount of functionalized fullerenes to a patient suffering from a fungal infection. The material comprising functionalized fullerenes can be administered topically as a fluid or a powder, by ingestion, or by injection.

Other embodiments of the invention are directed to dosage forms for treatment of fungal infections of a patient by a material comprising functionalized fullerenes. The dosage form can include a solution, a suspension or an emulsion where the dosage form can be used for topical, ingestible or injectable administration according to embodiments of the invention. Another embodiment of the invention is a dosage form where the material comprising functionalized fullerenes is included within a solid capsule or pellet for ingestible administration.

BRIEF DESCRIPTION OF DRAWING

FIG. 1 shows growth of *Aspergillus niger* on a) control, b) $TiO_2$ coated, and c) $TiO_2$+PHF coated tiles after 3 days of incubation in dark at room temperature and 90% relative humidity.

DETAILED DISCLOSURE

Embodiments of the invention are directed to functionalized fullerenes as antifungal agents. The functionalized fullerenes can be polyhydroxy fullerenes or other functionalized fullerenes. Some embodiments of the invention are directed to methods for treating and/or preventing fungal growth on the surface of an object by applying a material comprising a plurality of novel biocompatible antifungal functionalized fullerenes to a surface in an effective amount. The surface can be that of any indoor or outdoor structure, cloth or apparel, fruits, vegetables, harvested grains, plants, plant seeds, or any other item that can be colonized or infected by fungi.

Other embodiments of the invention are directed to a method for treating fungal diseases by administration of a dosage form having an effective amount of functionalized fullerenes in a vehicle to a patient that is effective yet non-toxic. The patient can be an animal, including mammals, birds, reptiles or amphibians. Mammalian species include humans, domesticated animals (including livestock and pets) and wild animals. Birds include poultry, exotic pets and wild birds. Dosage forms for the delivery of functionalized fullerenes include, but are not limited to, dermal, nasal, pulmonary, and intravitreal routes. The dosage form can be administered by: injection from a syringe with a needle or cannula; topical administration as drops, ointments or creams; or inhalation using a device such as a metered dose inhaler, dry powder inhaler or nebulizer. Advantageously, the fast and efficient treatments of fungal species according to embodiments of the invention are simple, non-toxic, and do not require illumination to activate the antifungal activity of functionalized fullerenes.

Various dosage forms can be used depending on the condition to be treated. One dosage form may be useful for preventing the fungal condition from occurring in a patient that may be predisposed to the fungal disease or anticipates exposure to the fungi. Another dosage form may be appropriate for inhibiting the condition in a patent that has the fungal disease in a state of arresting development or remission. Other dosage forms may be appropriate to relieve the fungal disease, cause regression of the disease, reduction of symptoms, or inhibit recurrence of the disease. Fungal diseases that can be addressed include any internal and external fungal infections to patients, including, but not exclusive to, athletes' foot, aspergillosis, coccidioidomycosis, histoplasmosis, blastomycosis, onychomycosis, tineapedis, tineamanus, and tineacorporis.

Fullerenes, as used herein, are from the general class of molecules that exists essentially in the shape of a three dimensional polyhedron containing from 20 to 1500 carbon atoms where carbon atoms are the predominant atomic moiety from which they are composed. The fullerenes include, but are not limited to, C-28, C-32, C-44, C-50, C-58, C-60, C-70, C-84, C-94, C-250 and C-540. (According to this nomenclature, the fullerene which contains 60 carbon atoms is denoted C-60, the fullerene which contains 70 carbon atoms is denoted C-70, etc.) Effective amounts of the functional fullerenes are the amounts sufficient to elicit the desired fungal growth inhibition or destruction by weight or by volume of a solution or dispersion comprising the functionalized fullerenes. As known to those skilled in the art, because of the nanoscale size of functionalized fullerenes, as well as their solubility in polar and non-polar solvents, the terms such as "dissolve," "disperse" and "suspend" can be interchangeable herein, as can be "solution," "dispersion" and "suspension," as in some cases it is not readily apparent that for the liquid phase employed if a true solution or a suspension is formed. In some embodiments of the invention, as is obvious to one skilled in the art, a solution and dispersion are distinct entities. The effective amount of functionalized fullerenes, or formulation thereof, may inhibit the fungal growth and/or ameliorate the severity of symptoms and/or complications associated with a fungal disease. The inhibition or amelioration in symptom and/or complication severity may be a 5%, 10%, 15%, 20%, 25%, 30%, 35%, 40%, 45%, 50%, 55%, 60%, 65%, 70%, 75%, 80%, 85%, 90%, 95%, 98%, or 99% decrease in severity.

Functionalized fullerenes include fullerenes ($C_x$ where x is 20 to 1500) with side groups attached to the outer surface of the cage via covalent bonds, ionic bonds, Dewar coordination, or Kubas interactions, or any combination thereof. The side groups can be either inorganic, including, but not exclusive to, OH, Br, $H_2$, Gd, Ti; organic, including, but not exclusive to, $C(COOH)_2$; or any combination of organic and/or inorganic functional groups. An effective functionalized fullerene for antifungal activity is a polyhydroxy fullerene. The number of functional groups attached per cage of fullerene can vary from 1 to a majority of the number of carbons in the fullerene cage. Also included among the functionalized fullerenes for purposes of the invention are the substituted fullerenes. These are fullerenes in which one or more of the atoms which comprise the fullerene cage structure is replaced by an atom other than carbon, such as nitrogen, boron or titanium, yet essentially retain the geometry of a polyhedron upon being so substituted. Also included among the functionalized fullerenes are endohedral fullerenes in which atoms of elements other than carbon (e.g., iron and gadolinium) reside inside the cage structure. Functionalized fullerenes have different physical and chemical properties based on the type and number of side groups, endohedral elements, and substituted elements. The functionalized fullerenes have dimensions that can be in excess of a nanometer in diameter, and can be considered nanoparticles.

Formulations that can be used according to embodiments of the invention include functionalized fullerenes and additionally: carriers, matrices, additives, or excipients as needed. These other components of the formulations can be organic gases, liquids or solids; inorganic gases, liquids, or solids; a polymer or polymer composite; water, an aqueous solution or aqueous suspension; a metal or metal alloy; a glass or ceramic; a biological or biologically derived material or any mixture of these materials. The functionalized fullerenes can be used in conjunction with other antifungal agents. Proportions of the functionalized fullerenes and other components can be varied depending upon factors including: solubility; chemical nature of the components; desired method of application or administration; and to conform to standard chemical or medical practices. For example, functionalized fullerenes can be locally administered to inhibit the fungal growth using a formulation having about 0.002 mg/L fullerene in a solvent, for example, water.

The functionalized fullerenes according to embodiments of the invention may be formulated for pharmaceutical administration for a variety of dosage forms. For example, functionalized fullerenes may be formulated to be suitable for topical administration; administration in an eye or ear; rectal or vaginal administration; as nose drops; for inhalation; as an injectable; or for oral administration. The functionalized fullerenes of the subject invention can be formulated according to any known methods for preparing pharmaceutically useful compositions. Formulations are disclosed in a numerous well known and readily available documents. For example, *Remington's Pharmaceutical Science* (Martin E W Easton Pa., Mack Publishing Company, $19^{th}$ ed.) discloses formulation methods that can be used in connection with embodiments of the invention. Formulations suitable for parenteral administration include, for example: aqueous sterile injection solutions, which may contain antioxidants, buffers, bacteriostats, other solutes and solvents that render the formulation isotonic with the blood of the intended recipient; and aqueous or nonaqueous sterile suspensions, which may include suspending agents and thickening agents. The formulations may be provided in unit-dose or multi-dose containers, for example sealed ampoules and vials, and may be stored in a freeze dried (lyophilized) condition requiring only a sterile liquid carrier, for example, water for injections. Extemporaneous injection solutions and suspensions may be prepared from sterile powder, granules, tablets, or other soluble or suspendable forms. It should be understood that in addition to the ingredients particularly mentioned above, the formulations of the subject invention can include other agents conventional in the art for the type of dosage form required by an embodiment of the invention.

In one embodiment of the invention, functionalized fullerenes can be applied as a component of a coating on a substrate or incorporated within a substrate to inhibit the growth of fungi on the substrate. Common antifungal coating applications include coatings on tiles, shingles, stucco, and interior or exterior surfaces of buildings to prevent growth of fungi (mold and mildew). For example, functionalized fullerenes can also be applied as antifungal coatings on various surfaces in hospitals to reduce the incident of nosocomial (hospital-acquired) infections. Functionalized fullerenes are soluble in polar (e.g., polyhydroxy fullerenes in water) as well as non-polar solvents (e.g., fullerene hydride in toluene). Therefore, the coating process can be facilitated by selecting appropriate solvents.

In one embodiment of the invention, functionalized fullerenes are mixed with photocatalysts. Among the photocatalysts that can be used for the practice of the invention are particles of titanium oxide, anatase titanium oxide, brookite titanium oxide, strontium titanate, tin oxide, zinc oxide, iron oxide, and mixtures thereof. Particulate photocatalysts can range in size from about 2 to 500 nm cross section or diameter, with an average diameter or cross section of 2 to 100 nm. The particles can be spherical or any other shape. Preferably, the functionalized fullerene is polyhydroxy fullerene and photocatalyst is $TiO_2$. More preferably, the mass ratio of $TiO_2$ to polyhydroxy fullerenes in the mixture is about 100:1. Under such conditions, the dark antifungal action can be further enhanced in the light.

In another embodiment of the invention, functionalized fullerenes can be applied as coatings on food, such as fruits, bread and vegetables, to prevent or delay the onset of fungal growth where the functionalized fullerenes are nontoxic and biocompatible. Examples of such fullerenes include but are not limited to polyhydroxy fullerenes and carboxy fullerenes, which are known for therapeutic and toxicological properties, and are currently included in some cosmetic formulations. Nontoxic and biocompatible fullerenes can also be incorporated in foods as additives or preservatives to prolong the storage-life of perishables.

In yet another embodiment of the invention, functionalized fullerenes can be applied as coatings for use in agriculture. The functionalized fullerenes can be mixed with nutrients and other chemicals as sprayable solutions to prevent fungal disease in plants.

The need for new antifungal agents is further exacerbated by emerging pathogens and antibiotic resistant fungi. In one embodiment of the invention, functionalized fullerenes can serve as an antifungal preparation that simultaneously is useful as a non-biological antimycotic or antibiotic drug. In another embodiment of the invention, the functionalized fullerenes can be coated on or incorporated with other nanoparticles or nanostructures to provide antifungal properties while improving the efficacy of drugs by controlled release or targeted delivery.

Methods and Materials

Inhibition of Fungi

Experiments were conducted with functionalized fullerene comprising antifungal coatings on tiles. A first set of three tiles was coated with titanium dioxide ($TiO_2$) where 100 µL of 0.1 wt % $TiO_2$ was applied to the surface of each tile using a pipette and spreading the solution over the tile's surface with the pipette's tip. A second set of three tiles was coated with a mixture of $TiO_2$ and polyhydroxy fullerenes where 100 µL of a 100:1 $TiO_2$:PHF (0.1 wt % $TiO_2$) suspension was applied to the surface of each tile using a pipette and spreading the solution over the tile's surface with the pipette's tip. A third set of four tiles served as control. Tryptic soy broth was applied to all tiles to promote the growth of fungi. All tiles were subsequently inoculated with 100 µL of *Aspergillus niger* from a stock suspension containing $1\times10^6$ colony forming units (CFU)/mL. The tiles were incubated for three days in the dark at room temperature and a controlled relative humidity of 90%. The fungal growth after three days on representative tiles is shown in FIG. 1, which clearly illustrates that the presence of polyhydroxy fullerenes prevented the growth of fungi on those tiles so coated.

Determination of Minimum Inhibitory Concentration of Functionalized Fullerenes

Experiments were conducted in a 96-well plate to determine the minimum inhibitory concentration of polyhydroxy fullerenes using a standard micro-dilution protocol (Rodriguez-Tudela et al., *European Society of Clinical Microbiology and Infectious Diseases*, E. Dis 7.1, 2003). Standard media for testing fungal growth (RPMI 1640 amended with 2% glucose) was employed. PHF concentrations from 500 mg/L to 0.002 mg/L were tested in duplicate. *A. niger* was inoculated at a concentration of $3\times10^5$ CFU/mL. The 96-well plate, wrapped in aluminum foil, was then incubated in an orbital shaker at 37° C. and 100 rpm. Absorbance measurements were taken 405 nm, 450 nm, 490 nm and 650 nm, after 24 hours and 48 hours of incubation. The results indicate that the minimum concentration of PHF required to inhibit fungal growth by 50% is less than 0.002 mg/L.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A method of reducing mold and mildew growth characterized by growth of *Aspergillus Niger* on a surface, comprising the steps of:

providing a material comprising an effective amount of functionalized fullerenes, wherein said functionalized fullerenes consist of fullerenes ($C_x$ where x is 20 to 1500) attached to at least one functional group at one to a majority of the carbons in the fullerene, wherein said functional groups are selected from the group consisting of OH, Br, H, Gd, Ti, and $C(COOH)_2$, and wherein at least one of the functional groups is OH; and distributing said material comprising functionalized fullerenes over the surface, wherein said material reduces mold or mildew growth in the dark.

2. The method of claim 1, wherein said functionalized fullerenes are endohedral fullerenes, substituted fullerenes, surface functionalized fullerenes, or any mixtures thereof.

3. The method of claim 1, wherein said material further comprises a solvent comprising water or an organic liquid.

4. The method of claim 1, wherein said material further comprises one or more carriers, matrices, additives, excipients or combinations thereof.

5. The method of claim 1, wherein said surface is of a fruit, vegetable, harvested grains, plants, or plant seeds.

6. The method of claim 1, wherein said surface is of an architectural structure, furniture, or a vehicle.

7. A method of treating a fungal disease characterized by growth of *Aspergillus Niger* in a patient, comprising the steps of:

providing a material comprising an effective amount of functionalized fullerenes, wherein said functionalized fullerenes consist of fullerenes ($C_x$ where x is 20 to 1500) attached to at least one functional group at one to a majority of the carbons in the fullerene, wherein said functional groups are selected from the group consisting of OH, Br, H, Gd, Ti, and $C(COOH)_2$, and wherein at least one of the functional groups is OH; and administering said material to the patient, wherein said material reduces mold or mildew growth in the dark.

8. The method of claim 7, wherein said functionalized fullerenes are endohedral fullerenes, substituted fullerenes, surface functionalized fullerenes, or any mixtures thereof.

9. The method of claim 7, wherein said material further comprises a solvent comprising water or an organic liquid.

10. The method of claim 7, wherein said step of administering comprises injecting, ingesting or applying topically as a fluid or a powder.

11. The method of claim 7, wherein said patient is an animal selected from a group consisting of mammals, birds, reptiles and amphibians.

\* \* \* \* \*